US006943160B2

(12) United States Patent
Branch et al.

(10) Patent No.: US 6,943,160 B2
(45) Date of Patent: Sep. 13, 2005

(54) MORPHOLINE DERIVATIVES AS ANTAGONISTS OF OREXIN RECEPTORS

(75) Inventors: Clive Leslie Branch, Harlow (GB); Christopher Norbert Johnson, Harlow (GB); Alexander B. Smith, Harlow (GB); Geoffrey Stemp, Harlow (GB); Kevin Thewlis, Harlow (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 10/432,421

(22) PCT Filed: Nov. 22, 2001

(86) PCT No.: PCT/EP01/13687

§ 371 (c)(1),
(2), (4) Date: Oct. 9, 2003

(87) PCT Pub. No.: WO02/44172

PCT Pub. Date: Jun. 6, 2002

(65) Prior Publication Data

US 2004/0058921 A1 Mar. 25, 2004

(30) Foreign Application Priority Data

Nov. 28, 2000 (GB) ............................................. 0028955
Jun. 12, 2001 (GB) ............................................. 0114291

(51) Int. Cl.$^7$ .................. A61K 31/5377; C07D 413/06; C07D 413/12; C07D 413/14; C07D 417/06
(52) U.S. Cl. ............................... 514/235.2; 514/236.8; 544/128; 544/131; 544/133
(58) Field of Search ................................ 544/169, 133; 514/231.5, 237.5

(56) References Cited

U.S. PATENT DOCUMENTS

| | | | | |
|---|---|---|---|---|
| 4,870,074 A | * | 9/1989 | Kon et al. ................ | 514/233.8 |
| 4,923,863 A | * | 5/1990 | Scopes et al. ............ | 514/235.5 |
| 5,604,225 A | | 2/1997 | Manfred et al. .......... | 514/230.8 |
| 5,719,147 A | * | 2/1998 | Dorn et al. .............. | 514/227.5 |
| 5,922,706 A | * | 7/1999 | Dorn et al. .............. | 514/227.5 |
| 6,506,750 B1 | * | 1/2003 | Ducoux et al. .......... | 514/235.8 |
| 6,596,730 B1 | * | 7/2003 | Coulton et al. ............. | 514/300 |
| 6,635,661 B2 | * | 10/2003 | Cuny et al. ................. | 514/331 |
| 6,677,332 B1 | * | 1/2004 | Cuny et al. ............. | 514/212.02 |
| 6,677,354 B2 | * | 1/2004 | Branch et al. ............... | 514/318 |
| 6,699,879 B1 | * | 3/2004 | Coulton et al. ............. | 514/313 |
| 6,703,392 B2 | * | 3/2004 | Aissaoui et al. ....... | 514/252.04 |
| 2004/0058923 A1 | * | 3/2004 | Ancliff et al. ........... | 514/237.8 |

FOREIGN PATENT DOCUMENTS

| | | | | |
|---|---|---|---|---|
| WO | WO 00/47577 | 8/2000 | ................ | 514/313 |
| WO | WO 00/47580 | 8/2000 | ................ | 514/300 |
| WO | WO 01/68609 | 9/2001 | ............ | 514/252.04 |
| WO | WO 2003051368 A1 | * 6/2003 | ....... | A61K/31/4525 |

OTHER PUBLICATIONS

Voisin, T. et al., "Orexins and their receptors: structural aspects and role in peripheral tissues," Cell Mol. Life Sci., 60: 72–87 (2003) at p. 72 1st column; 79, 1st column; and p. 84, 2nd column.*

Hungs, Marcel and Mignot, Emmanuel, "Hypocretin/orexin, sleep and narcolepsy," BioEssays 23(5): 397–408 (May 2001) at p. 398, 2nd column.*

Taylor, Meghan and Shaw, Willis, "The other side of the orexins: endocrine and metabolic actions," Am. J. Physiol. Endocrinol. Metab., 284: E13–E17 (Jan. 2003) at p. E16, 1st column.*

Nishino, Seiji, et al., "Low Cerebrospinal Fluid Hypocretin (Orexin) and Altered Energy Homeostasis in Human Narcolepsy," Ann. Neurol., 50: 381–388 (Sep. 2001) at p. 382, 1st column. PubMed ID: 11558795.*

Nishino, Seiji, "The hypocretin/orexin system in health and disease," Biol. Psychiatry, 54(2): 87–95 (Jul. 15, 2003)(abstract only).*

Salomon, Ronald, et al., "Diurnal variation of cerebrospinal fluid hypocretin–1 )Orexin–A) levels in control and depressed subjects," Biol. Psychaitry 54(2): 96–104 (Jul. 15, 2003)(abstract only). PubMed ID: 12873798.*

Allen, R.P., et al., "Increased CSF hypocretin–1 (orexin–A) in restless legs syndrome," Neurology 59(4): 639–41 (Aug. 27, 2002)(abstract only). PubMed ID: 12196669.*

Hirose, Masaaki, et al., "N–acyl 6,7–dimethoxy–1,2,3,4–tetrahydroisquinoline: The first orexin–2 receptor selective non–peptidic antagonist," Bioorganic & Medicinal Chem. Letters 13(24): 4497–4499 (Dec. 15, 2003).*

Langmead, C.J., et al., "Characterization of the binding of [3H]–SB–674042, a novel nonpeptide antagonist, to the human orexin–1 receptor," Br. J. Pharmacol. 141(2): 340–6 (Jan. 2004)(abstract only). PubMed ID: 14691055.*

Kato, Shiro, et al., "Novel benzamides as selective and potent gastrokinetic agents," J. Med. Chem. 34(2):616–24 (1991); Reg. No. 112885–36–6.*

Kato, Shiro, et al., "Synthesis and biological activity of 4–amino–5–chloro–2–ethoxy–3–hydroxybenzamides, metabolites of a new gastroprokinetic agent, mosapride," Chem. & Pharma. Bull. 44(8):1484–1492. Reg. No. 182068004, 182068048, 182068128, 1820681511.*

Cummings, Jeffrey L., "Alzheimer's Disease," N. Engl. J. Med. 351:56–67 (Jul. 1, 2004) at pp. 56–60.*

Bullock, Roger, "Future directions in the treatment of Alzheimer's disease," Expert Opin. Invest. Drugs 13(4): 303–314 (2004) at pp. 303, 306–309.*

(Continued)

Primary Examiner—Kamal A. Saeed
Assistant Examiner—Anthony J. Paviglianiti
(74) Attorney, Agent, or Firm—Kathryn L. Sieburth; Mary E. McCarthy; Charles M. Kinzig

(57) ABSTRACT

This invention relates to morpholine derivatives of formula (I) and their use as antagonists of orexin receptors.

13 Claims, No Drawings

OTHER PUBLICATIONS

Robinson, Stephen R., et al., "Lessons from the AN 1792 Alzheimer vaccine: lest we forget," Neurobiol. of Aging 25(5): 609–615 (May–Jun. 2004) at pp. 609–610.*

Lammers et al., "Pharmacological Management of Narcolepsy". *Expert Opin. Pharmacother.*, 4(10): 1739–1746 (2003).

George et al., "Hypocretin (Orexin) Pathway to Sleep". *The Lancet*, 355: pp. 6 (2000).

Nishino, et al., "Hypocretin (Orexin) Deficiency in Human Narcolepsy". *The Lancet*, 355: 39–40 (2000).

Samuel Klein. "The War Against Obesity: Attacking a New Front". *Am. J. Clin. Nutr.*, 69: 1061–1063 (1999).

Sakurai et al., "Orexins and Orexin Receptors: A Family of Hypothalamic Neuropeptides and G Protein–Coupled Receptors that Regulate Feeding Behavior". *Cell*, 92: 573–585 (1998).

* cited by examiner

MORPHOLINE DERIVATIVES AS ANTAGONISTS OF OREXIN RECEPTORS

This is a 371 of International Application PCT/EP01/13687, filed Nov. 22, 2001, which claims benefit of the following Great Britain Applications: GB 0028955.3, filed Nov. 28, 2000 and GB 0114291.8, filed Jun. 12, 2001.

This invention relates to morpholine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; bum pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell*, 1998, 92, 573–585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides morpholine derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders, and/or stroke, particularly ischemic or haemorrhagic stroke.

International Patent Applications WO99/09024, WO99/58533, WO00/47577, and WO00/47580, disclose phenyl urea derivatives and WO00/47576, discloses quinolinyl cinnamide derivatives as orexin receptor antagonists.

According to the invention there is provided a compound of formula (I):

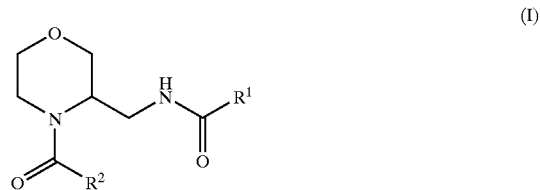

wherein:

R[1] is phenyl, naphthyl, a mono or bicyclic heteroaryl group containing up to 3 heteroatoms selected from N, O and S; any of which may be optionally substituted;

$R^2$ represents phenyl or a 5- or 6-membered heteroaryl group containing up to 3 heteroatoms selected from N, O and S, wherein the phenyl or heteroaryl group is substituted by $R^3$, and further optional substituents; or $R^2$ represents an optionally substituted bicyclic aromatic or bicyclic heteroaromatic group containing up to 3 heteroatoms selected from N, O and S;

$R^3$ represents an optionally substituted $(C_{1-4})$alkoxy, halo, optionally substituted $(C_{1-6})$alkyl, optionally substituted phenyl, or an optionally substituted 5- or 6-membered heterocyclic ring containing up to 3 heteroatoms selected from N, O and S;

or a pharmaceutically acceptable derivative thereof.

Examples of groups where $R^1$ is a mono or bicyclic heteroaryl group containing up to 3 heteroatoms selected from N, O and S, include pyridyl, furanyl, indolyl, benzofuranyl, quinolinyl, isoquinolinyl, pyrazinyl, quinoxalinyl, benzoxazolyl, pyrazolyl and isoxazolyl.

Preferably $R^1$ is an optionally substituted phenyl, benzofuranyl, quinolinyl, indolyl or benzoxazolyl. The group may have up to 5, preferably 1, 2 or 3 optional substituents.

Examples of groups where $R^2$ represents a 5- or 6-membered heteroaryl group containing up to 3 heteroatoms selected from N, O and S, include thiazolyl, pyrazolyl, triazolyl, pyridazyl and isoxazolyl.

Preferably when $R^2$ represents phenyl, or a 5- or 6-membered heterocyclyl group the substituent $R^3$ is adjacent to the point of attachment to the amide carbonyl group.

Preferably $R^2$ represents optionally substituted thiazolyl. Particular $R^2$ groups incorporating the $R^3$ substituent, that may be mentioned are 4-(2-methyl-5-(4-fluorophenyl))thiazolyl, 4-(2-methyl-5-(3-fluorophenyl))thiazolyl, 4-(2-methyl-5-(2-fluorophenyl))thiazolyl, and 4-(2-methyl-5-phenyl)thiazolyl, specifically 4-(2-methyl-5-(4-fluorophenyl))thiazolyl.

$R^3$ may be a trifluoromethoxy group, halo, $(C_{4-6})$alkyl, optionally substituted phenyl or an optionally substituted 5- or 6-membered heterocyclyl ring contains up to 3 heteroatoms selected from N, O and S.

Examples of groups where $R^3$ is a 5- or 6-membered heterocyclyl group containing up to 3 heteroatoms selected from N, O and S, include furanyl, thienyl, pyrrolyl, oxazolyl, thiazolyl, imidazolyl, oxadiazolyl, thiadiazolyl, pyridyl, triazolyl, triazinyl, pyridazyl, pyrimidinyl, isothiazolyl, isoxazolyl, pyrazinyl or pyrazolyl.

More preferably $R^3$ represents trifluoromethoxy, methoxy, halo, or optionally substituted phenyl, pyridyl, pyrazolyl or oxadiazolyl group.

Even more preferably $R^3$ represents an optionally substituted phenyl, e.g. 4-fluorophenyl.

Alternatively $R^3$ represents a pyridyl group.

Optional substituents for the groups $R^1$ to $R^3$ include halogen, hydroxy, oxo, cyano, nitro, $(C_{1-4})$alkyl, $(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$alkyl, hydroxy$(C_{1-4})$alkoxy, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$ alkylsulfonyloxy, $(C_{1-4})$alkylsulfonyl$(C_{1-4})$alkyl, arylsulfonyl, arylsulfonyloxy, arylsulfonyl$(C_{1-4})$alkyl, $(C_{1-4})$ alkylsulfonamido, $(C_{1-4})$alkylamido, $(C_{1-4})$ alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$ alkyl, arylcarboxamido$(C_{1-4})$alkyl, aroyl, aroyl$(C_{1-4})$alkyl, or aryl$(C_{1-4})$alkanoyl group; a group $R^aR^bN-$, $R^aOCO(CH_2)_r$, $R^aCON(R^4)(CH_2)_r$, $R^aR^bNCO(CH_2)_r$, $R^aR^bNSO_2(CH_2)_r$ or $R^aSO_2NR^b(CH_2)_r$ where each of $R^a$ and $R^b$ independently represents a hydrogen atom or a $(C_{1-4})$alkyl group or where appropriate $R^aR^b$ forms part of a $(C_{3-6})$ azacyloalkane or $(C_{3-6})$(2-oxo)azacycloalkane ring and r represents zero or an integer from 1 to 4.

Preferred substituents are $(C_{1-4})$alkyl, $(C_{1-4})$alkoxy, either of which may be optionally substituted, halogen and cyano.

In addition $R^1$ may be optionally substituted by a phenyl ring optionally substituted by a halogen, cyano, or $C_{1-4}$alkanoyl or $C_{1-4}$alkylsulfonyl group; or by a 5- or 6-membered heterocyclic ring, optionally substituted by a $(C_{1-2})$alkyl or $R^aR^bN$-group; wherein $R^a$ and $R^b$ are as defined above.

In the groups $R^1$ to $R^3$, substituents positioned ortho to one another may be linked to form a fused ring, e.g. giving a group which is 2,3-ethylenedioxyphenyl.

When a halogen atom is present in the compound of formula (I) it may be fluorine, chlorine, bromine or iodine.

When the compound of formula (I) contains an alkyl group, whether alone or forming part of a larger group, e.g. alkoxy or alkylthio, the alkyl group may be straight chain, branched or cyclic, or combinations thereof, it is preferably methyl or ethyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolic or residue thereof.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and salts thereof. The following schemes detail synthetic routes to compounds of the invention.

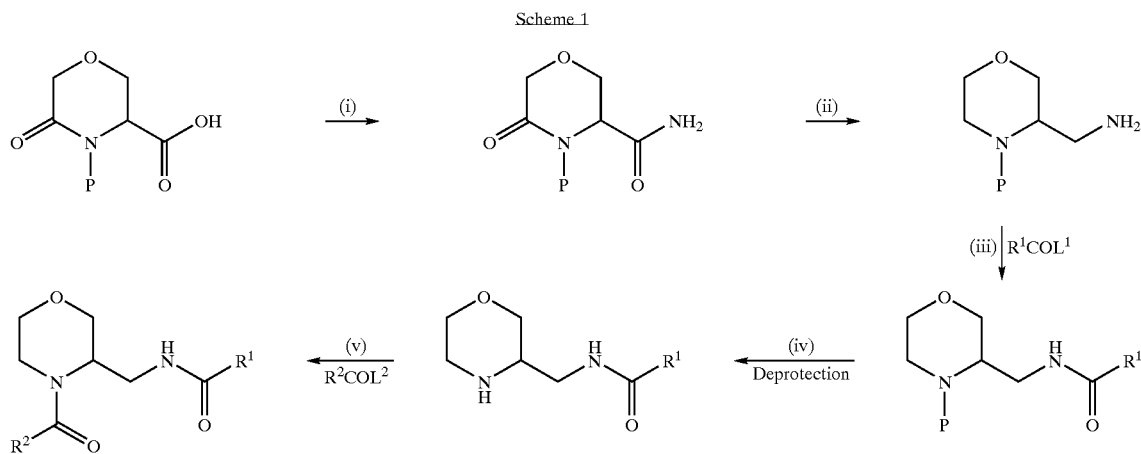

wherein $R^1$ and $R^2$ are as defined for formula (I), P is a protecting group and $L^1$ and $L^2$ are leaving groups.

An example of a protecting group P is optionally substituted benzyl. Deprotection conditions for step (iv) conveniently utilises catalytic hydrogenolysis in an inert solvent (e.g. using palladium on charcoal in a lower alcohol or ethyl acetate).

Examples of suitable leaving groups $L^1$ and $L^2$ include halogen, hydroxy, OC(=O)alkyl OC(=O)O-alkyl and OSO$_2$Me. Steps (iii) and (v) may be carried out using a wide range of known acylation conditions, e.g. in an inert solvent such as dichloromethane, in the presence of a base such as triethylamine. Alternatively these steps may be carried out when $L^1$ or $L^2$ represents hydroxy, in which case the reaction takes place in an inert solvent such as dichloromethane in the presence of a diimide reagent such as 1-ethyl-3-(3-dimethylaminopropyl)carbodiimide hydrochloride, and an activator such as 1-hydroxybenzotriazole.

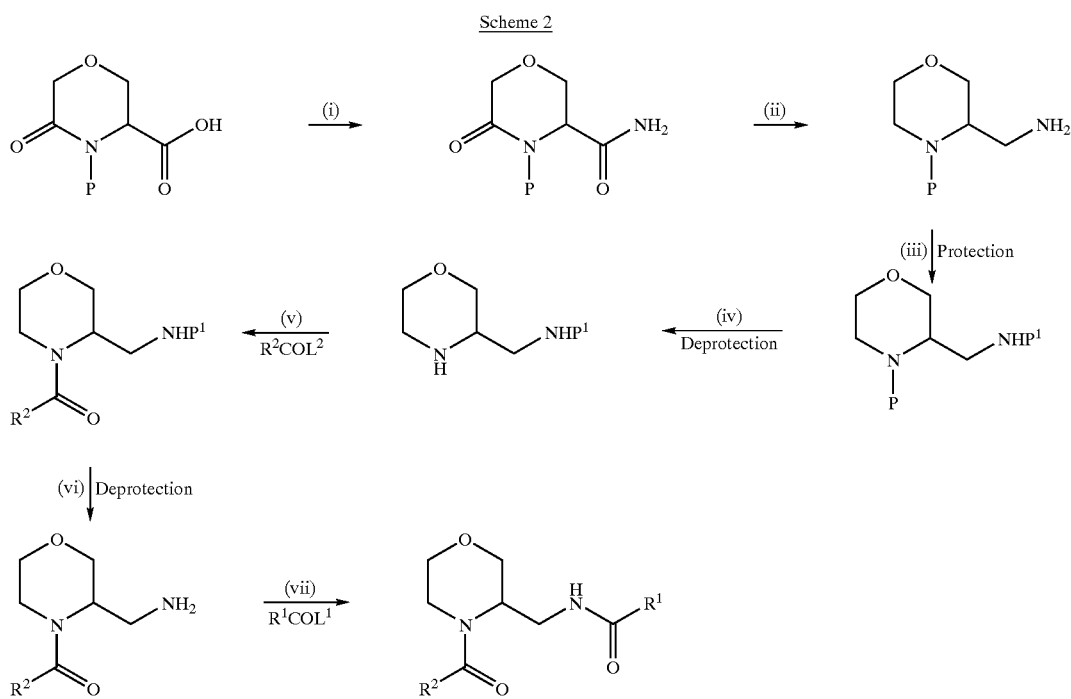

wherein $R^1$ and $R^2$ are as defined for formula (I), P and $P^1$ are amino protecting groups as described for Scheme 1 and $L^1$ and $L^2$ are leaving groups as described for Scheme 1.

Examples of protecting groups P and $P^1$ include t-butyloxycarbonyl, trifluoroacetyl, benzyloxycarbonyl and optionally substituted benzyl. Deprotection conditions, step (iv) and (vi), will depend on the particular protecting group; for the groups mentioned above these are respectively, acid (e.g. trifluoroacetic acid in dichloromethane), base (e.g. potassium carbonate in a solvent such as aqueous methanol) and catalytic hydrogenolysis in an inert solvent (e.g. using palladium on charcoal in a lower alcohol or ethyl acetate). In scheme 2, protecting groups P and $P^1$ are selected to be different.

The starting materials for use in the processes of Schemes 1 and 2 are commercially available, known in the literature or can be prepared by known methods. Within the schemes above there is scope for functional group interconversion.

Schemes 1 and 2 illustrate the synthesis of racemic compounds of formula (I), from (RS)-4-benzyl-5-oxomorpholine-3-carboxuylic acid which may be synthesisied from (DL)-serine as described in G. R. Brown, A. J. Foubister and B. Wright, *J. Chem Soc. Perkin Trans. I*, 1985, 2577. Starting from (D)- or (L)-serine, synthetic methods known to those skilled in the art may be used to give single enantiomers of the compounds of formula (I).

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable derivatives thereof.

Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human orexin receptor is required such as obesity and diabetes; prolactinoma; hypoprolactinemia; hypothalamic disorders of growth hormone deficiency; idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; bulimia and hypopituitarism. The compounds of formula (I) or pharmaceutically acceptable derivatives thereof are also useful in the treatment of stroke, particularly ischaemic or haemorrhagic stroke.

The compounds of formula (I) and their pharmaceutically acceptable derivatives are particularly useful for the treatment of obesity, including obesity associated with Type 2 diabetes, and sleep disorders. Additionally the compounds are useful for the treatment of stroke.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required.

The invention also provides the use of a compound of formula (I), or a pharmaceutically acceptable derivative thereof, in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parentally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human orexin-A has the amino acid sequence as in SEQ ID NO: 1: pyroEPLPDCCRQKTCSCRLYELLHGAGNHAAGILTL-NH$_2$.

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, Drosophila or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1–D8 illustrate the preparation of intermediates to compounds of the invention.

Abbreviation used herein are as follow:
MDC represents methylene dichloride
THF represents tetrahydrofuran
DMSO represents methyl sulphoxide Description 1: (RS)-4-Benzyl-3-carboxamido-5-oxomorpholine To (RS)-4-benzyl-5-oxo-morpholine-3-carboxylic acid (2.0 g, 8.51 mmol) in MDC (40 ml) was slowly added oxalyl chloride (1.51 ml, 17.1 mmol). The mixture was stirred for 0.5 h at room temperature and then evaporated to give (RS)-4-benzyl-5-oxomorpholine-3-carbonyl chloride as a brown solid (1.99 g, 92%). Ammonia gas was bubbled steadily through a solution of (RS)-4-benzyl-5-oxomorpholine-3-carbonyl chloride (1.99 g, 7.79 mmol) in MDC (40 ml) at 0° C. for 0.5 h, and then the mixture allowed to warm to room temperature. The solid was collected by filtration, washed with MDC (30 ml) and dried in vacuo at 40° C. to give the title compound as a white solid (2.1 g, 99%). Mass spectrum (API$^+$): Found 235 (MH$^{30}$ ). $C_{12}H_{14}N_2O_3$ requires 234.

Description 2: (RS)-3-Aminomethyl-4-benzylmorpholine

Lithium aluminium hydride (1M in THF) (20 ml, 20 mmol) was added to a stirred solution of D1 (1.0 g, 4.27 mmol) in anhydrous THF (30 ml). The resultant mixture was stirred at ambient temperature for 24 hours, then water (0.76 ml), 8% NaOH (1.5 ml) and water (0.76 ml) were slowly added sequentially. The aqueous was extracted with diethyl ether (3×20 ml) and the extracts dried (Na$_2$SO$_4$) and evaporated to give the title compound as a clear gum (0.79 g, 89%). Mass spectrum (API$^+$): 207 (MH$^+$). C$_{12}$H$_{18}$N$_2$O requires 206.

Description 3: (RS)-4-Benzyl-3-(2-methoxybenzamidomethyl)morpholine

To a solution of D2 (500 mg, 2.43 mmol) was added triethylamine (1 ml, 7.29 mmol) followed by 2-methoxybenzoyl chloride (455 mg, 2.67 mmol). The resulting solution was stirred for 0.75 h at room temperature, then washed with saturated aqueous sodium hydrogen carbonate, dried (Na$_2$SO$_4$) and evaporated in vacuo. The residue was chromatographed on silica gel using 30–100% ethyl acetate in hexane gradient elution to give the title compound as a colourless oil (678 mg, 82%). Mass spectrum (API$^+$): 341 (MH$^+$). C$_{20}$H$_{24}$N$_2$O$_3$ requires 340.

Description 4: (RS)-3-(2-Methoxybenzamidomethyl)morpholine

To a solution of D3 (1.12 g, 3.29 mmol) in ethanol (160 ml) was added 10% palladium on carbon paste (1.20 g). The mixture was hydrogenated at 20 psi overnight at room temperature. Filtration through kieselguhr and evaporation in vacuo gave the title compound as a dark gum (0.795 g, 96%). Mass spectrum (API$^+$): 251 (MH$^+$). C$_{13}$H$_{18}$N$_2$O$_3$ requires 250.

Description 5: (RS)-4-Benzyl-3-(t-butyloxycarbonylaminomethyl)morpholine

A solution of di-t-butyl dicarbonate (1.20 g, 5.49 mmol) in MDC (5 ml) was added dropwise, with ice cooling, to a stirred solution of D2 (1.13 g, 5.49 mmol) in MDC (30 ml). The resulting solution was stirred overnight at room temperature, washed with saturated aqueous sodium hydrogen carbonate and the organic layer evaporated in vacuo. The residue was purified on silica gel eluting with ethyl acetate/hexane mixtures to give the title compound as a colourless gum (1.68 g, 100%). Mass spectrum (API$^+$): 307 (MH$^+$). C$_{17}$H$_{26}$N$_2$O$_3$ requires 306.

Description 6: (RS)-3-(t-Butyloxycarbonylaminomethyl)morpholine

To a solution of D5 (1.68 g, 5.82 mmol) in ethanol (200 ml) was added 10% palladium on carbon paste (1.80 g). The mixture was hydrogenated at 20 psi overnight at room temperature. Filtration through kieselguhr and evaporation in vacuo gave the title compound as a colourless oil (1.16 g, 92%). Mass spectrum (API$^+$): Found 217 (MH$^+$). C$_{10}$H$_{20}$N$_2$O$_3$ requires 216.

Description 7: (RS)-3-(t-Butyloxycarbonylaminomethyl)-4-((4-(2-methyl-5-(4-fluorophenyl))thiazolyl)carbonyl)morpholine 2-Methyl-5-(4-fluorophenyl)thiazole-4-carbonyl chloride (1.73 g, 6.75 mmol) in MDC (20 ml) was added to a solution of D6 (1.16 g, 5.37 mmol) and triethylamine (2.24 ml, 16.1 mmol) in MDC (80 ml) and the mixture stirred at ambient temperature overnight. The reaction mixture was washed with saturated aqueous sodium hydrogen carbonate (50 ml). The organic layer was evaporated in vacuo and the resultant residue chromatographed on silica gel eluting with ethyl acetate/hexane mixtures to give the title compound as a golden oil (0.73 g, 31%). Mass spectrum (API$^+$): 436 (MH$^+$). C$_{21}$H$_{26}$FN$_3$O$_4$S requires 435.

Description 8: (RS)-3-(Aminomethyl)-4-((4-(2-methyl-5-(4-fluorophenyl))thiazolyl)carbonyl)morpholine A solution of D7 (730 mg, 1.68 mmol) in MDC (15 ml) and trifluoroacetic acid (1.5 ml) was stirred at 40° C. for 0.5 h. The solution was evaporated, and the resulting oil dissolved in 0.5M HCl (20 ml) and washed twice with ethyl acetate (20 ml). The aqueous phase was basified to pH 14 with aqueous NaOH, then extracted with MDC (3×50 ml). The combined organic extracts were dried (Na$_2$SO$_4$) and evaporated to a colourless gum (462 mg, 82%). Mass spectrum (API$^+$): 336 (MH$^+$). C$_{16}$H$_{18}$FN$_3$O$_2$S requires 335.

EXAMPLE 1

(RS)-3-(2-Methoxybenzamidomethyl)-4-((4-(2-methyl-5-phenyl))thiazolyl)carbonyl)morpholine A mixture of D4 (30 mg, 0.12 mmol), 2-methyl-5-phenylthiazole-4-carbonyl chloride (31 mg, 0.13 mmol), and triethylamine (36 mg, 0.35 mmol) in MDC (5 ml) was shaken for 1 h. The resultant solution was washed with saturated aqueous sodium hydrogen carbonate (6 ml). The organic layer was applied directly onto a dry 10 g pre-packed silica cartridge and eluted with 30–100% ethyl acetate in hexane to give the title compound as an off white solid (32 mg, 60%). Mass spectrum Electrospray LC MS): Found 452 (MH$^+$). C$_{24}$H$_{25}$N$_3$O$_4$S requires 451.

EXAMPLE 2

(RS)-3-((4-Benzofuranyl)carbonylaminomethyl)-4-((4-(2-methyl-5-(4-fluoro-phenyl))thiszolyl)carbonyl)morpholine A mixture of D8 (30 mg, 0.09 mmol), benzofuran-4-carboxylic acid (20 mg, 0.12 mmol), 1-(3-dimethylaminopropyl)-3-ethyl carbodiimide hydrochloride (17 mg, 0.09 mmol) and 1-hydroxybenzotriazole (10 mg) in MDC (5 ml) was shaken for 20 h. The resulting solution was washed with saturated aqueous sodium hydrogen carbonate (6 ml). The organic layer was applied directly onto a dry 10 g pre-packed silica cartridge and eluted with 30–100% ethyl acetate in hexane, then 2–20% methanol in ethyl acetate to give the title compound as an off-white solid (31 mg, 72%). Mass spectrum (Electrospray LC MS): Found 480 (MH$^+$). C$_{25}$H$_{22}$FN$_3$O$_4$S requires 479.

The compounds of the examples below were prepared from the appropriate amine and acid using similar procedures to those described above.

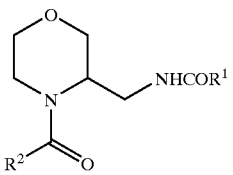
| Example | R¹ | R² | Mass Spectrum (Electrospray LC/MS) |
|---|---|---|---|
| 3 | 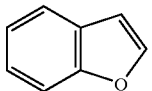 | 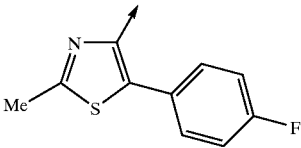 | Found 480 (MH⁺) $C_{25}H_{22}FN_3O_4S$ requires 479. |
| 4 | 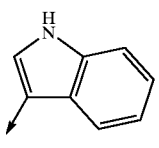 | 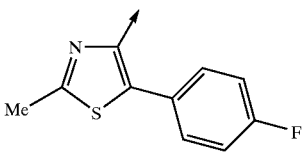 | Found 479 (MH⁺) $C_{25}H_{23}FN_4O_3S$ requires 478. |
| 5 | 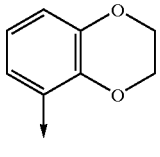 | 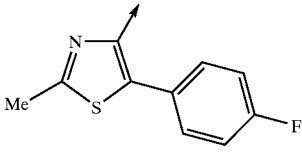 | Found 498 (MH⁺) $C_{25}H_{24}FN_3O_5S$ requires 497. |
| 6 | 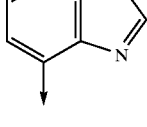 | 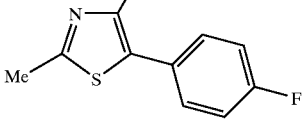 | Found 495 (MH⁺) $C_{25}H_{23}FN_4O_4S$ requires 494. |
| 7 | 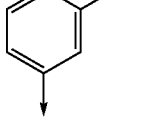 | 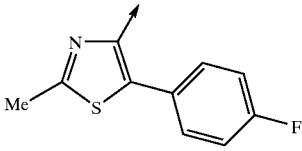 | Found 524 (MH⁺) $C_{24}H_{21}F_4N_3O_4S$ requires 523. |
| 8 | 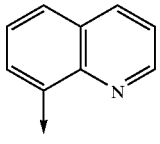 | 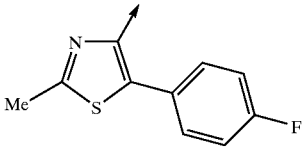 | Found 491 (MH⁺) $C_{26}H_{23}FN_4O_3S$ requires 490 |
| 9 | 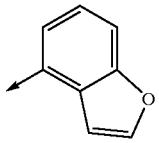 | 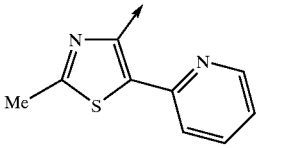 | Found 463 (MH⁺) $C_{24}H_{22}N_4O_4S$ requires 462 |
| 10 | 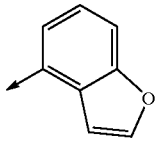 | 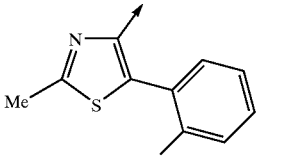 | Found 480 (MH⁺) $C_{25}H_{22}FN_3O_4S$ requires 479 |

-continued

| Example | R¹ | R² | Mass Spectrum (Electrospray LC/MS) |
|---|---|---|---|
| 11 | benzofuran-4-yl | 2-methyl-5-(3-fluorophenyl)thiazol-4-yl | Found 480 (MH⁺) $C_{25}H_{22}FN_3O_4S$ requires 479 |
| 12 | benzofuran-4-yl | 5-phenylthiazol-4-yl | Found 448 (MH⁺) $C_{24}H_{21}N_3O_4S$ requires 447 |

EXAMPLE 13

(RS)-3-(2-Methoxybenzamidomethyl)-4-((4-(2-methyl-5-(4-fluorophenyl))thiazolyl)carbonyl) morpholin A mixture of D4 (50 mg, 0.20 mmol), 2-methyl-5-(4-fluorophenyl)thiazole-4-carboxylic acid (52 mg, 0.22 mmol), 1-(3-dimethylaminopropyl)-3-ethylcarbodiimide hydrochloride (38 mg, 0.20 mmol) and 1-hydrochloride (38 mg, 0.20 mmol) and 1-hydroxybenzotriazole (10 mg) in MDC (5 ml) was shaken for 20 h. The resultant solution was washed with saturated aqueous sodium hydrogen carbonate (6 ml). The organic layer was applied directly onto a dry 10 g pre-packed silica cartridge and eluted with 30–100% ethyl acetate in hexane to give the title compound as an off white solid (53 mg, 57%). Mass spectrum (Electrospray LC MS): Found 470 (MH⁺). $C_{24}H_{24}FN_3O_4S$ requires 469.

It is to be understood that the present invention covers all combinations of particular and preferred subgroups described herein above.

Determination of Orexin-1 Receptor Antagonist Activity

The orexin-1 receptor antagonist activity of the compounds of formula (I) was determined in accordance with the following experimental method.

Experimental Method

HEK293 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 µl/well into 96-well black clear bottom sterile plates from Costar which had been precoated with 10 µg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 90 min at 37° C. in 5% $CO_2$. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, TiPS, 1995, 16, 413–417) to generate a concentration effect value. Antagonist Kb values were calculated using the equation:

$$K_b = IC_{50}/(1+([3/EC_{50}]))$$

where $EC_{50}$ was the potency of human orexin-A determined in the assay (in nM terms) and $IC_{50}$ is expressed in molar terms.

Compounds of Examples tested according to this method had pKb values ≧6.8 at the human cloned orexin-1 receptor. The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/ML G418 Sulphate from GIBCO BRL and 10% heat inactivated fetal calf serum from Gibco BRL. The cells were seeded at 20,000 cells/100 µl/well into 96-well black clear bottom sterile plates from Costar which had been pre-coated with 10 µg/well of poly-L-lysine from SIGMA. he seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 60 min at 37° C. in 5% $CO_2$. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, *TiPS*, 1995, 16, 413–417) to generate a concentration effect value. Antagonist Kb values were calculated using the equation:

$$Kb = IC50/(1+([3/EC50])$$

where EC50 was the potency of human orexin-A determined in the assay (in nM terms) and IC50 is expressed in molar terms.

Compounds of Examples tested according to this method had pKb values in the range 6.1–7.4. at the human cloned orexin-2 receptor.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

We claim:

1. A compound of formula (I):

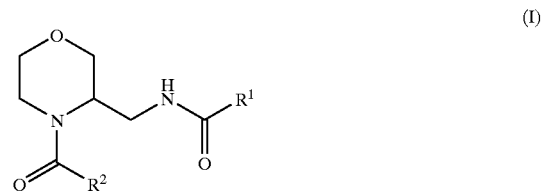

wherein:

R[1] is phenyl, naphthyl, a mono or bicyclic heteroaryl group containing up to 3 heteroatoms selected from N, O and S; any of which may be optionally substituted;

R[2] represents phenyl or a 5- or 6-membered heteroaryl group containing up to 3 heteroatoms selected from N, O and S, wherein the phenyl or heteroaryl group is substituted by R[3], and further optional substituents; or R[2] represents an optionally substituted bicyclic aromatic or bicyclic heteroaromatic group containing up to 3 heteroatoms selected from N, O and S;

$R^3$ represents an optionally substituted $(C_{1-4})$alkoxy, halo, optionally substituted $(C_{1-6})$alkyl, optionally substituted phenyl, or an optionally substituted 5- or 6-membered heterocyclic ring containing up to 3 heteroatoms selected from N, O and S;

or a pharmaceutically acceptable salt thereof.

2. A compound according to claim 1 wherein $R^1$ is an optionally substituted phenyl, benzofuranyl, quinolinyl, indolyl or benzoxazolyl.

3. A compound according to claim 1 wherein $R^2$ represents an optionally substituted thiazolyl.

4. A compound according to claim 1, wherein $R^3$ represents an optionally substituted phenyl or pyridyl group.

5. A pharmaceutical composition comprising the compound of formula (I) according to claim 1, or a pharmaceutically acceptable salt thereof, and a pharmaceutically acceptable carrier.

6. A method of treating a disease or disorder selected from the group: obesity, obesity associated with diabetes, a sleep disorder, sleep apnea, narcolepsy, insomnia, parasomnia jet-lag syndrome, ischemic stroke and hemmorhagic stroke where an antagonist of a human orexin receptor is required, which comprises administering to a subject in need thereof an effective amount of the compound of formula (I) according to claim 1, or a pharmaceutically acceptable salt thereof.

7. A compound selected from the group:
(RS)-3-(2-Methoxybenzamidomethyl)-4-((4-(2-methyl-5-phenyl)thiazolyl)carbonyl)morpholine,
(RS)-3-((4-Benzofuranyl)carbonylaminomethyl)-4-((4-(2-methyl-5-(4-fluorophenyl))thiazolyl)carbonyl)morpholine,
(RS)-3-(2-Methoxybenzamidomethyl)-4-((4-(2-methyl-5-(4-fluorophenyl))thiazolyl)carbonyl)morpholine,
and a pharmaceutically acceptable salt of any one thereof.

8. A compound having the formula:

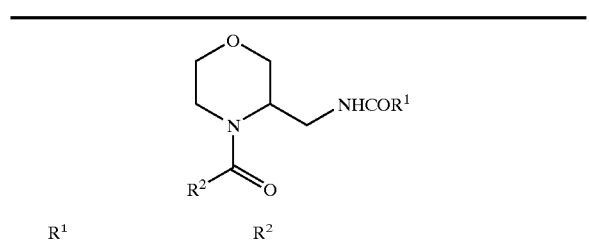

| $R^1$ | $R^2$ |
|---|---|
| 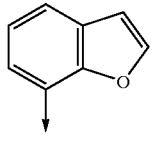 | 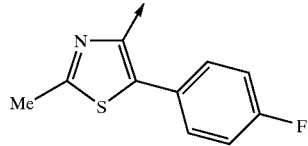 |
| 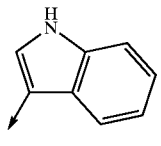 | 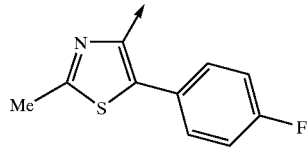 |

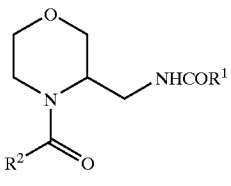

| $R^1$ | $R^2$ |
|---|---|
| 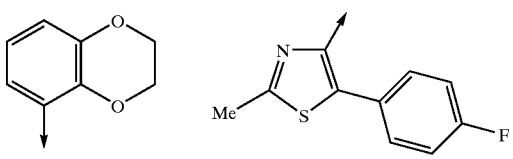 | |
| 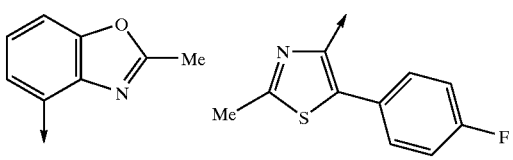 | |
| 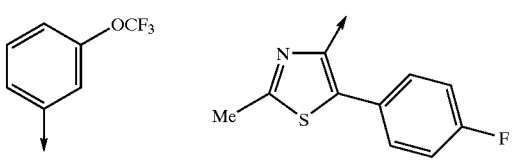 | |
| 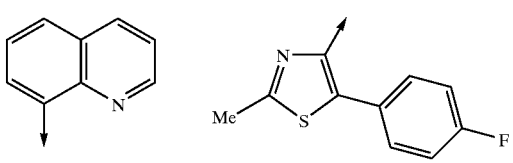 | |
| 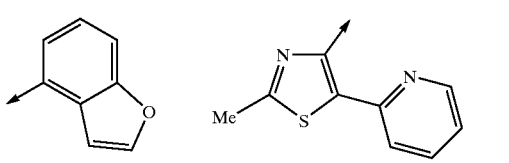 | |
| 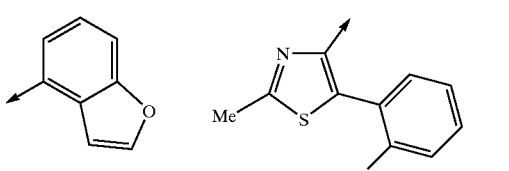 | |
| 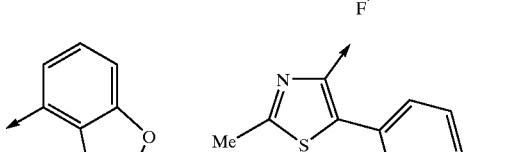 | |
| 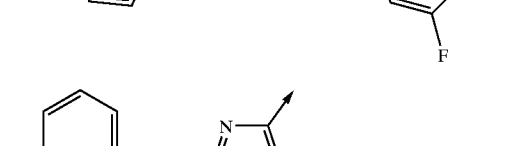 | | or a pharmaceutically acceptable salt of any one thereof.

9. A pharmaceutical composition comprising the compound according to claim 7, or a pharmaceutically acceptable salt thereof, and a pharmaceutically acceptable carrier.

10. A pharmaceutical composition comprising the compound according to claim 8, or a pharmaceutically acceptable salt thereof, and a pharmaceutically acceptable carrier.

11. A method of treating a disease or disorder selected from the group: obesity, obesity associated with diabetes and sleep disorder, where an antagonist of a human orexin receptor is required, which comprises administering to a subject in need thereof an effective amount of the compound according to claim 7, or a pharmaceutically acceptable salt thereof.

12. A method of treating a disease or disorder selected from the group: obesity, obesity associated with diabetes and sleep disorder, where an antagonist of a human orexin receptor is required, which comprises administering to a subject in need thereof an effective amount of the compound according to claim 8, or a pharmaceutically acceptable salt thereof.

13. A method of treating a disease or disorder selected from the group: obesity, obesity associated with diabetes and a sleep disorder where an antagonist of a human orexin receptor is required, which comprises administering to a subject in need thereof an effective amount of the compound of formula (I) according to claim 1, or a pharmaceutically acceptable salt thereof.

* * * * *

SEQUENCE LISTING

```
<160> NUMBER OF SEQ ID NOS: 1

<210> SEQ ID NO 1
<211> LENGTH: 35
<212> TYPE: PRT
<213> ORGANISM: Homo Sapien

<400> SEQUENCE: 1

Glu Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu Asn His
        35
```